United States Patent
Masutani et al.

(10) Patent No.: US 6,673,948 B2
(45) Date of Patent: Jan. 6, 2004

(54) FLUORINATED OXETANE DERIVATIVES AND PRODUCTION PROCESS THEREOF

(75) Inventors: Tetsuya Masutani, Settsu (JP); Akinori Yamamoto, Settsu (JP)

(73) Assignee: Daikin Industries, Ltd., Osaka (JP)

(*) Notice: Subject to any disclaimer, the term of this patent is extended or adjusted under 35 U.S.C. 154(b) by 0 days.

(21) Appl. No.: 10/221,193

(22) PCT Filed: Mar. 13, 2001

(86) PCT No.: PCT/JP01/01939

§ 371 (c)(1), (2), (4) Date: Sep. 23, 2002

(87) PCT Pub. No.: WO01/74799

PCT Pub. Date: Oct. 11, 2001

(65) Prior Publication Data

US 2003/0065199 A1 Apr. 3, 2003

(30) Foreign Application Priority Data

Mar. 31, 2000 (JP) ............................................ 2000-98923

(51) Int. Cl.[7] ............................................ C07D 305/06
(52) U.S. Cl. ....................................... 549/511; 549/510
(58) Field of Search .................................. 549/510, 511

(56) References Cited

FOREIGN PATENT DOCUMENTS

| | | |
|---|---|---|
| GB | 2 269 816 A | 2/1994 |
| JP | A 2000-191652 | 7/2000 |
| WO | WO 96/21657 | 7/1996 |

Primary Examiner—Ba K. Trinh
(74) Attorney, Agent, or Firm—Armstrong, Kratz, Quintos, Hanson & Brooks, LLP

(57) ABSTRACT

A process for preparing compounds of formula (I) comprising radical addition of RfI to 3-(allyloxy)methyl-3-alkyloxetane (1) wherein R is $C_{1-3}$ alkyl and Rf is $C_{1-18}$ linear or branched fluoroalkyl.

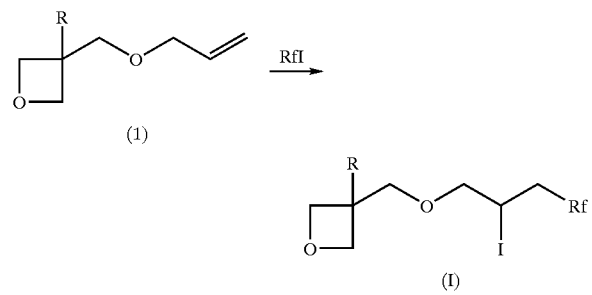

The compounds of formula (I) are useful as intermediates for preparing various fluorine-containing functional materials.

6 Claims, No Drawings

FLUORINATED OXETANE DERIVATIVES AND PRODUCTION PROCESS THEREOF

This application is a 371 of PCT/JP01/01939 filed on Mar. 13, 2001.

TECHNICAL FIELD

The present invention relates to oxetane derivatives having a fluorine-containing substituent on the side chain, and a production process thereof. The oxetane derivatives having a fluorine-containing substituent on the side chain are useful as intermediates for preparing various fluorine-containing functional materials.

BACKGROUND ART

A known method for synthesizing 3-fluoroalkoxymethyl-3-alkyloxetane is, for example, condensation of 3-bromomethyl-3-methyloxetane using a fluoroalkyl alcohol and an alkali (Japanese Unexamined Patent Publication No. 500422/1999). However, this method requires the use of expensive 3-bromomethyl-3-methyloxetane. In addition, there are some cases in which fluoroalkyl alcohols are not available. Therefore, the development of a more general-purpose synthetic method has been desired.

DISCLOSURE OF THE INVENTION

An object of the present invention is to provide a process for preparing 3-(3-fluoroalkylpropoxy)methyl-3-alkyloxetane.

Another object is to provide precursors thereof, i.e., 3-(3-fluoroalkylallyloxy)methyl-3-alkyloxetane and 3-(3-fluoroalkyl-2-iodopropoxy)methyl-3-alkyloxetane, and processes for their production.

The present inventors carried out experiments using the known compound 3-alkyl-3-(allyloxy)methyloxetane as a starting compound and found that radical addition of fluorinated alkane iodide to this compound can produce 3-(3-fluoroalkyl-2-iodopropoxy)methyl-3-alkyloxetane, which is an important intermediate in the preparation of oxetane compounds having a fluorine-containing substituent at the 3-position. The inventors further discovered that 3-(3-fluoroalkyl-2-iodopropoxy)methyl-3-alkyloxetane can be converted into 3-(3-fluoroalkylallyloxy)methyl-3-alkyloxetane under basic conditions, and that the resulting 3-(3-fluoroalkylallyloxy)methyl-3-alkyloxetane can further be converted into 3-(3-fluoroalkylpropoxy)methyl-3-alkyloxetane through a reduction reaction.

The features of the invention are shown in the following Scheme 1:

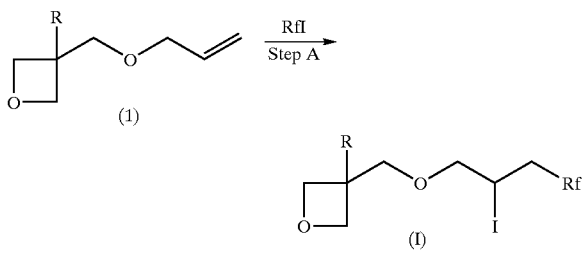

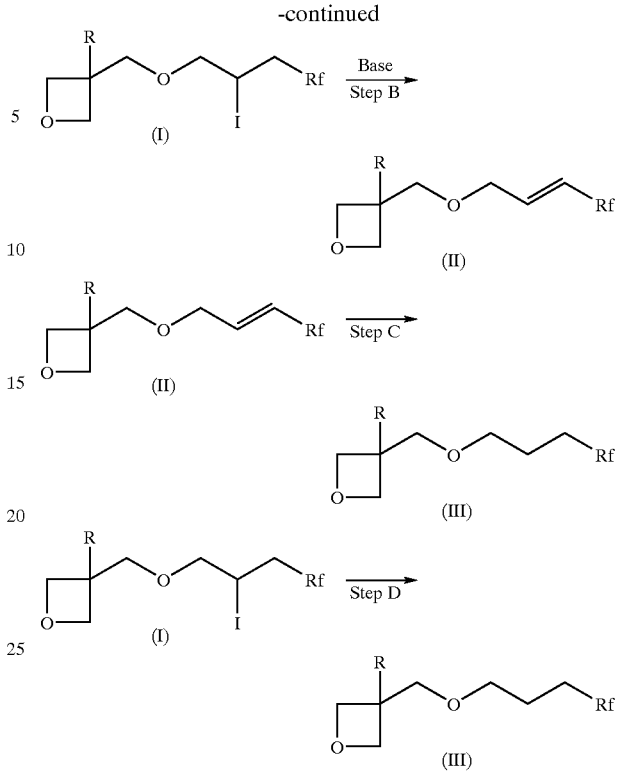

wherein R is $C_{1-3}$ alkyl and Rf is $C_{1-18}$ linear or branched fluoroalkyl.

The compound of formula (II) usually consists mainly of a trans isomer (E isomer) but may be a mixture of trans and cis isomers (E and Z isomers). In the invention, the compound of formula (II) is converted into the desired compound of formula (III) through the following reduction reaction.

The $C_{1-3}$ alkyl represented by R is methyl, ethyl, n-propyl or isopropy, preferably methyl or ethyl, more preferably methyl.

Rf is a $C_{1-18}$ linear or branched fluoroalkyl group having at least one fluorine atom. A greater number of fluorine atoms is more preferable. Rf is preferably a $C_{1-18}$ linear or branched perfluoroalkyl group such as $(CF_2)_nCF_3$ (wherein n is an integer of 0 to 17), perfluoroisopropyl, perfluoroisobutyl or perfluoro-t-butyl, more preferably $C_{2-18}$ perfluoroalkyl.

In the three-step reaction of the invention, it is important to maintain the reaction system under neutral or basic conditions not only during the reaction but also during the post-treatment because the oxetane ring is cleaved under acidic conditions, resulting in a failure to provide the desired compound.

The invention makes a variety of fluorinated alkane iodides available and thus enables the production of oxetane compounds having the desired fluorine-containing substituent on the side chain.

The starting compound of the invention, 3-alkyl-3-(allyloxy)methyloxetane (1), can easily be prepared by known methods, such as a method for synthesizing 3-(allyloxy)methyl-3-methyloxetane from 3-methyl-3-oxetanemethanol (J. Macromol. Sci.-Pure Appl. Chem. 2335, A34(1997)) and a method for synthesizing 3-(allyloxy)methyl-3-methyloxetane from 2-(allyloxy)methyl-2-methyl-1,3-propanediol (U.S. Pat. No. 2,924,607).

[Reaction Conditions for Step A]

In order to produce 3-(3-fluoroalkyl-2-iodopropoxy)methyl-3-alkyloxetane (I), the inventors used 3-alkyl-3-(allyloxy)methyloxetane (1) as a starting compound and tried to carry out an addition reaction in the presence of a radical initiator to add perfluoroalkyl iodide. As a result, it was found that this reaction proceeds to produce the desired product in good yield. Although the addition reaction of perfluoroalkyl iodide to an olefin in the presence of a radical initiator was a well-known reaction (general description: J. Fluorine Chem. 1, 93 (1999)), the addition of perfluoroalkyl iodide to 3-alkyl-3-(allyloxy)methyloxetane was unknown. In this addition reaction, avoiding the cleavage of the oxetane ring is important to produce the desired product in good yield. For this reason, a reaction under acidic conditions is not desirable. Since hydrogen iodide is readily removed from the resulting 3-(3-fluoroalkyl-2-iodopropoxy)methyl-3-alkyloxetane under basic conditions, basic conditions are not preferable except in the case that it is desired to obtain compound (II) immediately after the radical addition.

In the radical addition reaction, radical initiators such as azobisisobutyronitrile, benzoyl peroxide and t-butyl 2-ethylperhexanoate can be used or the reaction can be carried out by radical cleavage of perfluoroalkyl iodide caused by irradiation with light such as by a high pressure mercury lamp.

Although RfI can be reacted with 3-alkyl-3-(allyloxy)methyloxetane (1) in any molar ratio, it is preferable that RfI be used in an amount of 1 to 5 moles per mole of 3-alkyl-3-(allyloxy)methyloxetane (1). Although the amount of radical initiator used may vary depending on the kind of initiator, it is usually preferable that the initiator be used in an amount of 1 to 5 mole % relative to 3-alkyl-3-(allyloxy)methyloxetane (1).

The reaction temperature is in the range of about 50° C. to 80° C. and the reaction time is about 1 to 6 hours. The reaction can be performed in a solvent, for example, ethers such as diethyl ether and tetrahydrofuran, esters such as ethyl acetate, or aromatic hydrocarbons such as benzene and toluene.

[Reaction Conditions for Step B]

Next, a reaction to remove hydrogen iodide from 3-(3-fluoroalkyl-2-iodopropoxy)methyl-3-alkyloxetane (I) proceeds readily under basic conditions to produce 3-(3-fluoroalkylallyloxy)methyl-3-alkyloxetane (II). In this reaction, any appropriate base can be used. Basic conditions which are too strong, however, are not preferable because the reaction further proceeds to remove hydrogen fluoride from 3-(3-fluoroalkylallyloxy)methyl-3-alkyloxetane, giving a byproduct. Examples of useful bases include alkali metal hydroxides such as sodium hydroxide and potassium hydroxide, and alkali metal carbonates or hydrogencarbonates such as sodium carbonate, potassium carbonate, sodium hydrogencarbonate and potassium hydrogencarbonate. The base is preferably used in an amount of about 1 to 2 moles per mole of the starting 3-(3-fluoroalkyl-2-iodopropoxy)methyl-3-alkyloxetane (I). The reaction is preferably carried out at about room temperature and the reaction time is about 0.5 to 2 hours.

[Reaction Conditions for Step C]

Next, 3-(3-fluoroalkylallyloxy)methyl-3-alkyloxetane (II) is readily converted into 3-(3-fluoroalkylpropoxy)methyl-3-alkyloxetane (III) in the presence of a hydrogenation catalyst. Examples of useful hydrogenation catalysts include palladium/carbon powder, palladium/barium sulfate, platinum oxide and Raney nickel. The catalyst can be used, for example, in an amount of about 0.1 to 5 mass %, relative to the compound (II). Although the reaction proceeds satisfactorily at room temperature and atmospheric pressure, it is also possible to carry out the reaction with heating or under pressure. The reaction time is about 1 to 8 hours. Since reductive cleavage of the oxetane ring may occur under highly reductive conditions, the reaction should be carried out under conditions under which the oxetane ring is not cleaved. Examples of useful solvents include ethers such as tetrahydrofuran and dioxane, and alcohols such as methanol and ethanol.

[Reaction Conditions for Step D]

Another method for producing 3-(3-fluoroalkylpropoxy)methyl-3-alkyloxetane (III) comprises reducing 3-(3-fluoroalkyl-2-iodopropoxy)methyl-3-alkyloxetane (I) without performing the reaction to remove hydrogen iodide. Such reduction methods include hydrogenation using a reduction catalyst such as palladium/carbon powder, palladium/barium sulfate, platinum oxide or Raney nickel, or methods using a chemical reducing agent such as tributyltin hydride or lithium aluminum hydride. The reduction catalyst can be used, for example, in an amount of about 0.1 to 5 mass % relative to compound (I). The chemical reducing agent can be used, for example, in an amount of about 25 to 200 mole % relative to compound (I). The reaction temperature is in the range of about $-78°$ C. to $40°$ C. and the reaction time is about 1 to 4 hours. The reaction can be carried out in a solvent such as tetrahydrofuran, dioxane or like ethers.

The compounds of formulas (I), (II) and (III) prepared by the production process of the invention are useful as intermediates for preparing various fluorine-containing functional materials, such as resins and coating surface modifiers.

BEST MODE FOR CARRYING OUT THE INVENTION

Examples are given below to illustrate the invention in more detail, but it is to be understood that the invention is not limited thereto.

In the Examples, 3 m stainless steel columns packed with SE-30 were used in gas chromatography analysis, unless otherwise specified. NMR was measured with a Bruker 300 MHz spectrometer using chloroform-dl as a solvent.

REFERENCE EXAMPLE 1

Synthesis of 3-(allyloxy)methyl-3-methyloxetane 3-methyl-3-oxetane methanol (20.4 g), 50% aqueous sodium hydroxide solution (268 g), tetrabutylammonium chloride (2.8 g) and hexane (300 ml) were placed into a 500 ml flask and stirred at room temperature. After 19.4 g of allyl bromide was added dropwise, the reaction mixture was heated and refluxed for 2 hours. After completion of the reaction, the reaction mixture was filtered and separated into aqueous and organic phases. The aqueous phase was extracted with ethyl acetate and the extract was combined with the organic phase and washed with water. The solvent was distilled off using an evaporator, giving 17.2 g (61%) of product. The product was analyzed by gas chromatography and the results showed that the desired 3-(allyloxy)methyl-3-methyloxetane was obtained in a purity of 98%. Therefore, the product was used without purification for the following reaction.

$^1$H-NMR: 1.31(s,3H), 3.50(s,2H), 4.00(d,2H), 4.33(d,2H), 4.50(d,2H), 5.17(d,1H), 5.27(d,iH), 5.92(m,1H)

EXAMPLE 1

Radical Addition 3-(allyloxy)methyl-3-methyloxetan (7.1 g), nonafluorobutyl iodide (51.9 g) and azobisisobutyronitrile (0.245 g) were placed into a 100 ml flask and stirred at room temperature. Then the reaction mixture was heated to 70° C. and maintained at that temperature for 1 hour.

After completion of the reaction, nonafluorobutyl iodide was distilled off using an evaporator, giving 22.2 g of product. The product was analyzed by gas chromatography and the results showed that the desired 3-(4,4,5,5,6,6,7,7,7-nonafluoro-2-iodoheptyloxy)methyl-3-methyloxetane was obtained in a purity of 94%. Yield: 85%.

$^1$H-NMR 1.33(s,3H), 2.88(m,2H), 3.59(s,2H), 3.74(m, 2H), 4.38(d,2H), 4.41(m,1H), 4.52(d,2H)

$^{19}$F-NMR −81.6 ppm(3F), −114.4(2F), −125.1(2F), −126.4(2F)

EXAMPLE 2

Removal of Hydrogen Iodide 3-(4,4,5,5,6,6,7,7,7-nonafluoro-2-iodoheptoxy)methyl-3-methyloxetane (19.5 g) was placed into a 100 ml flask and stirred at room temperature. Then 25 ml of a methanol solution containing 4.2 g of potassium hydroxide was added dropwise and stirred overnight. The reaction mixture was filtered and washed with aqueous sodium thiosulfate solution and water and then dried over magnesium sulfate. The obtained product (8.5 g) was analyzed by gas chromatography and the results showed that the desired 3-(4,4,5,5,6,6,7,7,7-nonafluoro-2-heptenyloxy)methyl-3-methyloxetane was obtained in a purity of 93%. Yield: 59%.

The desired compound was obtained as a separable 78:22 (E:Z) mixture of geometric isomers. This mixture was separated by HPLC under the following conditions:

HPLC Conditions

Column: Fluofix 120N (Φ4.6*150 mm, product of Neos Co., Ltd.)

Mobile phase: Acetonitrile/water

Detection: UV(210 nm)

E-isomer $^1$H-NMR 1.27(s,3H), 3.50(s,2H), 4.14(m,2H), 4.33(d, 2H), 4.46(d,2H), 5.87(dt,1H), 6.43(m,1H)

$^{19}$F-NMR −82.1 ppm(3F), −112.8(2F), −125.2(2F), −126.7(2F)

Z-isomer $^1$H-NMR 1.25(s,3H), 3.46(s,2H), 4.28(m,2H), 4.33(d, 2H), 4.46(d,2H), 5.55(dt,1H), 6.26(m,1H)

$^{19}$F-NMR −82.1 ppm(3F), −112.8(2F), −125.5(2F), −126.7(2F)

EXAMPLE 3

Hydrogenation 3-(4,4,5,5,6,6,7,7,7-nonafluoro-2-heptenyloxy)methyl-3-methyloxetane (7.2 g) and 5% palladium/carbon powder were placed into a 100 ml flask and stirred at room temperature. After the flask was purged with nitrogen, hydrogen was circulated through the flask at about 60 ml/min for 4 hours. Then the reaction mixture was filtered through a celite column to remove the hydrogenation catalyst from the reaction solution. The obtained product (7.0 g) was analyzed by NMR and the results showed that the desired 3-(4,4,5,5,6,6,7,7,7-nonafluoro-2-heptyloxy)methyl-3-methyloxetane was obtained in a purity of 95%. Yield: 95%.

$^1$H-NMR 1.33(s,3H), 1.78(m,2H), 2.19(m,2H), 3.50(m, 2H), 3.59(s,2H), 4.38(d,2H), 4.52(d,2H)

$^{19}$F-NMR 81.6 ppm(3F), −114.4(2F), −125.1(2F), −126.4(2F)

INDUSTRIAL APPLICABILITY

According to the invention, the known compound 3-alkyl-3-(allyloxy)methyloxetane is used as a starting compound and a radical addition reaction is carried out to add fluorinated alkane iodide, thus giving 3-(3-fluoroalkyl-2-iodopropoxy)methyl-3-alkyloxetane, which is an important intermediate for oxetane compounds having a fluorine-containing substituent at the 3-position. Further, 3-(3-fluoroalkyl-2-iodopropoxy)methyl-3-alkyloxetane can be converted under basic conditions into 3-(3-fluoroalkylallyloxy)methyl-3-alkyloxetane, which can further be converted into 3-(3-fluoroalkylpropoxy)methyl-3-alkyloxetane through a reduction reaction.

What is claimed is:

1. A process for preparing a compound of formula (I) comprising radical addition of RfI to 3-(allyloxy)methyl-3-alkyloxetane (1) wherein R is $C_{1-3}$ alkyl and Rf is $C_{1-18}$ linear or branched fluoroalkyl,

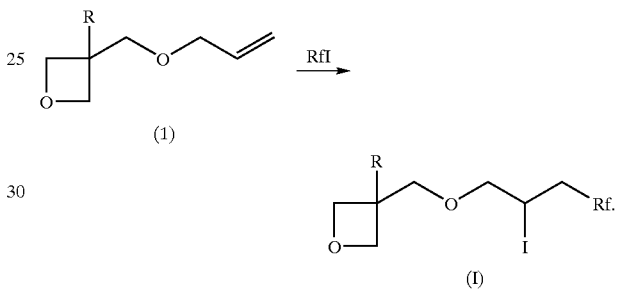

2. A process for preparing a compound of formula (II) comprising reacting the compound of formula (I) under basic conditions to remove hydrogen iodide therefrom wherein R is $C_{1-3}$ alkyl and Rf is $C_{1-18}$ linear or branched fluoroalkyl,

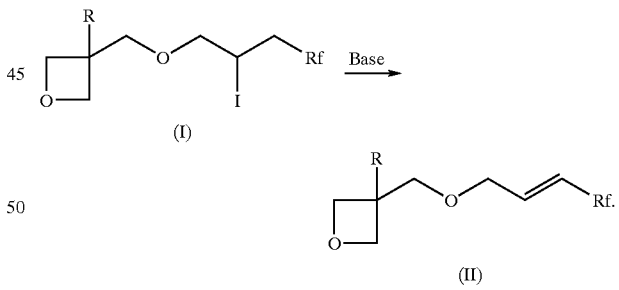

3. A process for preparing a compound of formula (III) comprising hydrogenating the compound of formula (II) in the presence of a hydrogenation catalyst wherein R is $C_{1-3}$ alkyl and Rf is $C_{1-18}$ linear or branched fluoroalkyl,

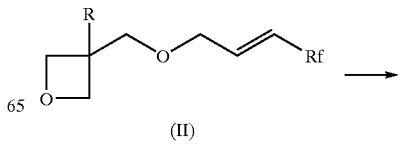

4. A process for preparing a compound of formula (III) comprising reducing the compound of formula (I) in the presence of a reduction catalyst or a reducing agent

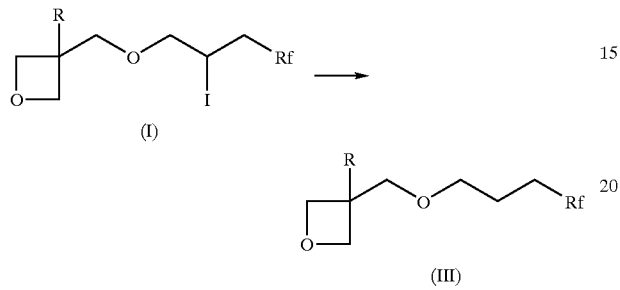

wherein R is $C_{1-3}$ alkyl and Rf is $C_{1-18}$ linear or branched fluoroalkyl.

5. A compound of the formula (I)

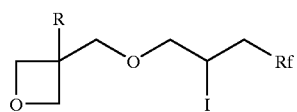

wherein R is $C_{1-3}$ alkyl and Rf is $C_{1-18}$ linear or branched fluoroalkyl.

6. A compound of the formula (II)

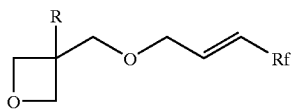

wherein R is $C_{1-3}$ alkyl and Rf is $C_{1-18}$ linear or branched fluoroalkyl.

* * * * *

UNITED STATES PATENT AND TRADEMARK OFFICE
CERTIFICATE OF CORRECTION

PATENT NO. : 6,673,948 B2
DATED : January 6, 2004
INVENTOR(S) : Matsutani et al.

It is certified that error appears in the above-identified patent and that said Letters Patent is hereby corrected as shown below:

Title page,
Item [30], Foreign Application Priority Data, change "Mar. 31, 2000   ((JP) ………….. 2000-98923" to be -- Mar. 31, 2000   ((JP) ………….. 2000-96923 --

Signed and Sealed this

First Day of June, 2004

JON W. DUDAS
*Acting Director of the United States Patent and Trademark Office*